(12) United States Patent
Nakashima et al.

(10) Patent No.: US 7,370,512 B2
(45) Date of Patent: May 13, 2008

(54) GAS ANALYZER APPARATUS

(75) Inventors: Tomohisa Nakashima, Inuyama (JP);
Naoki Tsukamoto, Inuyama (JP);
Motoki Ito, Inuyama (JP); Yukichika Ito, Inuyama (JP)

(73) Assignee: Energy Support Corporation, Aichi-ken (JP)

( * ) Notice: Subject to any disclaimer, the term of this patent is extended or adjusted under 35 U.S.C. 154(b) by 345 days.

(21) Appl. No.: 11/286,584

(22) Filed: Nov. 23, 2005

(65) Prior Publication Data

US 2006/0117832 A1    Jun. 8, 2006

(30) Foreign Application Priority Data

Dec. 2, 2004    (JP) .............................. 2004-349567
Mar. 16, 2005   (JP) .............................. 2005-075652

(51) Int. Cl.
*G01N 27/26* (2006.01)
(52) U.S. Cl. ..................................... 73/23.2
(58) Field of Classification Search ................ 73/23.2
See application file for complete search history.

(56) References Cited

U.S. PATENT DOCUMENTS

| | | | | |
|---|---|---|---|---|
| 4,875,990 A | | 10/1989 | Kodachi et al. | |
| 4,903,648 A | * | 2/1990 | Lassankse | ................. 123/65 R |
| 5,685,895 A | * | 11/1997 | Hagiwara et al. | ............. 96/117 |
| 5,836,155 A | * | 11/1998 | Katoh | .......................... 60/276 |
| 6,698,273 B2 | * | 3/2004 | Fujii | .............................. 73/37 |
| 2002/0162382 A1 | | 11/2002 | Fujii | |
| 2003/0084728 A1 | | 5/2003 | Boltz | |
| 2004/0058230 A1 | * | 3/2004 | Hsu | .............................. 429/62 |

FOREIGN PATENT DOCUMENTS

| | | |
|---|---|---|
| DE | 195 23 911 A1 | 1/1997 |
| JP | 61-13964 | 8/1981 |
| JP | 63-58152 | 3/1988 |

OTHER PUBLICATIONS

Mortimer A G et al, "Development of a robust electrochemical oxygen sensor", Sensors and Actuators B, Mar. 1995, pp. 328-335, vol. 24, No. 1-3.

* cited by examiner

*Primary Examiner*—Hezron Williams
*Assistant Examiner*—Rodney Frank
(74) *Attorney, Agent, or Firm*—Boyle Fredrickson,S.C.

(57) ABSTRACT

A gas analyzer apparatus including a support tube having a distal portion arranged in a flue and a gas sensor supported on the support tube. An air supply tube supplies cooling air into the support tube. A basal portion of the gas sensor is cooled by the cooling air.

13 Claims, 8 Drawing Sheets

GAS ANALYZER APPARATUS

BACKGROUND OF THE INVENTION

The present invention relates to a gas analyzer apparatus, and more particularly, to a flue gas analyzer apparatus for detecting and analyzing a predetermined chemical component contained in flue gas that flows through a flue.

To protect the global environment, flue gases emitted from combustion devices, such as internal combustion engines and combustion furnaces, are required to reduce their concentrations of nitrogen oxides. To satisfy this requirement, many flue gas analyzer apparatuses have been developed for detecting and analyzing nitrogen oxides contained in flue gases. The analysis results of a flue gas analyzer apparatus are reflected in combustion control for internal combustion engines and combustion furnaces to reduce concentrations of nitrogen oxides in their flue gases.

Known flue gas analyzer apparatuses include-direct-insertion type and gas-induction type flue gas analyzer apparatuses. A direct-insertion type flue gas analyzer apparatus is inserted in a flue at a measurement point to analyze the flue gas at that measurement point (refer to Japanese Laid-Open Patent Publication No. 63-58152). A gas-induction type flue gas analyzer apparatus induces flue gas sampled at a sampling point in a flue to a position distant from the sampling point and analyzes the flue gas at the distant position (refer to Japanese Examined Utility Model Publication No. 61-13964).

A direct-insertion type flue gas analyzer apparatus includes a probe for sampling the flue gas that flows in the flue. The probe is cylindrical and has a flange. The probe is inserted through a hole that is formed in an exhaust pipe (flue) of a combustion furnace etc. and is fixed to the exhaust pipe by means of its flange. A porous metal-sintered filter is arranged on a distal portion of the probe. A gas sensor is arranged in the probe at a position adjacent to the metal-sintered filter. A known solid electrolyte gas sensor uses a solid electrolyte formed from a ceramic such as zirconia. The flue gas that flows in the exhaust pipe is drawn into the probe through the metal-sintered filter. The gas sensor then performs detections on the gas in the probe. A terminal unit is arranged at a basal portion of the gas sensor. The terminal unit is electrically connected to an external control unit by lead wires.

A gas-induction type flue gas analyzer apparatus includes a gas sampling tube. The gas sampling tube includes a distal portion having a gas inlet and a basal portion having a gas outlet. The gas sampling tube is bypass-connected to an exhaust pipe. The distal portion of the gas sampling tube is arranged in the exhaust pipe. A solid electrolyte gas sensor is arranged in the gas sampling tube. The dynamic pressure of the gas that flows in the exhaust pipe causes gas to flow into the inlet of the gas sampling tube. The gas then comes into contact with the solid electrolyte gas sensor and then flows out of the outlet of the gas sampling tube so as to return to the exhaust pipe. A detection signal of the gas sensor is transmitted to an external meter through lead wires drawn out of a terminal unit.

In such conventional flue gas analyzer apparatuses, the distal portion of the probe or the gas sampling tube is arranged in or near the center of the exhaust pipe. This arrangement enables the flue gas analysis to be conducted without being affected by an eddy that is often generated at the inner surface of the exhaust pipe. The length of the portion of the probe or gas sampling tube inserted into the exhaust pipe is determined in accordance with the diameter of the exhaust pipe. Thus, the insertion length of the probe or the gas sampling tube in the exhaust pipe increases as the diameter of the exhaust pipe increases and decreases as the diameter of the exhaust pipe decreases. The gas-induction type flue gas analyzer apparatus simply requires the insertion length of the gas sampling tube in the exhaust pipe to be adjusted but does not require the position of the gas sensor to be changed. However, depending on the diameter of the exhaust pipe, the direct-insertion type flue gas analyzer apparatus, in which the gas sensor is arranged in the distal portion of the probe, may require the entire gas sensor, which includes its basal portion in which the terminal unit is arranged, to be arranged in the exhaust pipe.

To keep the lead wires drawn out from the terminal unit in a bundled state, a lead wire bundling cap is attached to the basal portion of the gas sensor. The lead wire bundling cap is a circular plate having a plurality of holes. The lead wire bundling cap is made, for example, from an elastic rubber material. The lead wires are drawn through the holes of the lead wire bundling cap. When the gas sensor is used in a high temperature environment, the lead wire bundling cap is easily damaged by heat.

To prevent heat damage to the lead wire bundling cap, materials having high heat resistance (e.g., ceramics or a metal material such as platinum) may be used to form the lead wire bundling cap. However, materials having high heat resistance are expensive. The use of such a material increases the costs of the components used in the flue gas analyzer apparatus. The flue gas analyzer apparatus is required to reduce heat damage of the basal portion of the gas sensor without increasing the component costs.

SUMMARY OF THE INVENTION

It is an object of the present invention to provide a gas analyzer apparatus that reduces heat damage of a basal portion of a gas sensor without increasing component costs of the gas analyzer apparatus.

One aspect of the present invention is a gas analyzer apparatus for use with a flue through which flue gas flows. The gas analyzer apparatus is provided with a support tube including a distal portion adapted to be arranged in the flue. A gas sensor detects a predetermined chemical component contained in the gas and includes a distal portion, fixed to the distal portion of the support tube, and a basal portion arranged in the support tube. An air supply means supplies cooling air for cooling the basal portion of the gas sensor into the support tube.

Other aspects and advantages of the present invention will become apparent from the following description, taken in conjunction with the accompanying drawings, illustrating by way of example the principles of the invention.

BRIEF DESCRIPTION OF THE DRAWINGS

The invention, together with objects and advantages thereof, may best be understood by reference to the following description of the presently preferred embodiments together with the accompanying drawings in which.

DETAILED DESCRIPTION OF THE PREFERRED EMBODIMENTS

A gas analyzer apparatus according to a first embodiment of the present invention will now be described with reference to FIGS. 1 and 5. A gas analyzer apparatus 11 of the first embodiment is connected to an exhaust pipe of a combustion device. Examples of the combustion device include an engine, a boiler, and an industrial furnace. The gas analyzer apparatus 11 detects and analyzes predetermined chemical components, such as oxygen and nitrogen oxides, contained in the exhaust gas (gas to be measured) that flows in the exhaust pipe. One example of the gas analyzer apparatus 11 is a flue gas analyzer apparatus, which is of a direct-insertion type, includes a gas sensor that is arranged in the vicinity of a measurement point in the exhaust pipe.

Figure 1:
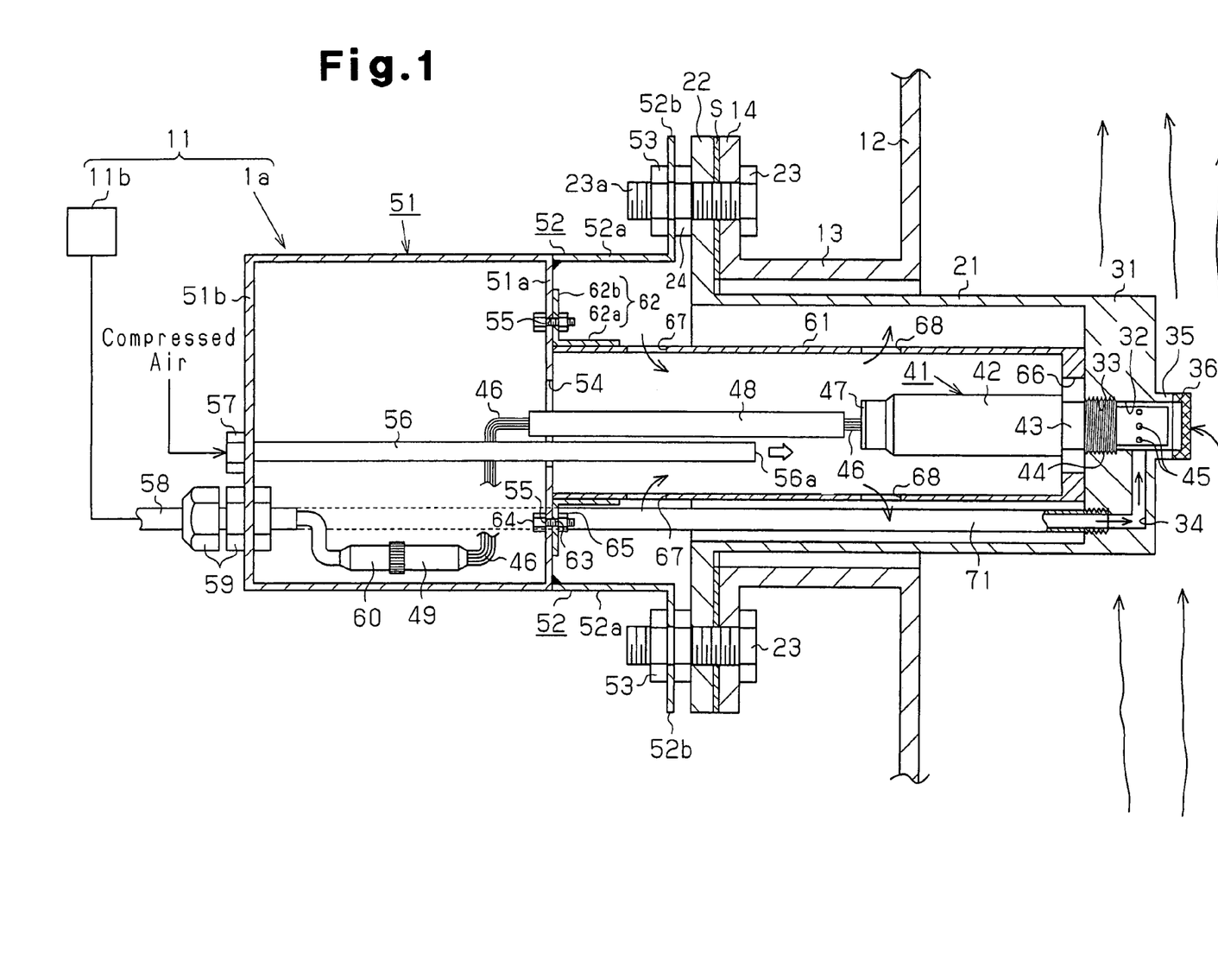
FIG. 1 is a cross-sectional view of a flue gas analyzer apparatus according to a first embodiment of the present invention.

As shown in FIG. 1, the flue gas analyzer apparatus 11 includes a transmitter 11a and an analyzer 11b. The transmitter 11a detects a predetermined chemical component contained in the flue gas that flows in the exhaust pipe 12 and transmits a detection signal. The analyzer 11b is electrically connected to the transmitter 11a. The analyzer 11b is arranged externally to the exhaust pipe 12. A reception tube 13 for receiving the transmitter 11a extends from the exhaust pipe 12. The reception tube 13 has an outer end with a flange 14. The transmitter 11a is fixed to the flange 14 when received in the reception tube 13. The transmitter 11a that is fixed in this way is partially exposed in a flue that is defined in the exhaust pipe 12.

The transmitter 11a will now be described. The transmitter 11a includes a support tube 21, or a cylindrical housing, having a basal end with a flange 22. The support tube 21 is received by the reception tube 13. Bolts 23 and nuts 24 fasten the flange 22 of the support tube 21 to the flange 14 of the reception tube 13. A seal S is arranged between the flanges 14 and 22 to prevent leakage of flue gas between the support tube 21 and the reception tube 13. Each bolt 23 includes a head, which is located at the side of the flange 14, and a threaded male portion 23a, which projects from an outer end surface of the nut 24 at the side of the flange 22.

The support tube 21 will now be described. The support tube 21 has a distal end wall 31 that is exposed in the flue. An accommodation channel 32 is formed in the distal end wall 31. A distal portion of a gas sensor 41 is received in and fixed to the accommodation channel 32. A threaded female portion 33 is formed in the surface defining the accommodation channel 32. The threaded female portion 33 extends into the accommodation channel 32 to a predetermined depth so that it is formed in only part of the of the distal end wall 31. Further, an L-shaped connecting channel 34 is formed in the distal end wall 31 to connect the interior of the support tube 21 and the accommodation channel 32.

The support tube 21 includes an annular filter support projection 35 extending from the distal end wall 31. A dust filter 36 is fixed to the filter support projection 35. The filter 36 is formed by sintering metal powder. The filter 36 is, for example, cup-shaped and has a rim, which comes into contact with the distal surface of the filter support projection 35 when the filter 36 is fixed to the filter support projection 35.

The gas sensor 41 will now be described. The gas sensor 41 includes a tubular sensor case 42. A sensor nut 43 is formed on the sensor case 42. A threaded male portion 44 is formed on the sensor case 42 at the distal side of the sensor nut 43. A plurality of gas inlets 45 are formed in the outer surface of the sensor case 42 at the distal side of the threaded male portion 44. The gas inlets 45 are formed at predetermined intervals in the circumferential direction of the sensor case 42. The distal portion of the sensor case 42 is received in the accommodation channel 32, and the threaded male portion 44 of the sensor case 42 is mated with the threaded female portion 33 of the accommodation channel 32 so as to fix the sensor case 42 to the distal end wall 31 of the support tube 21. In this manner, the gas sensor 41 is fixed. When the threaded male portion 44 is mated with the threaded female portion 33, movement of the gas sensor 41 in the distal direction is restricted as the sensor nut 43 comes into contact with the inner surface of the distal end wall 31.

The sensor case 42 accommodates a sensor element (not shown) that is operable under high temperatures and a sensor heater (not shown) for heating the sensor element. The sensor element is formed by a plate or a rod with oxygen ion conductive solid electrolyte.

A lead wire bundling cap 47 is attached to a basal portion of the sensor case 42. A plurality of lead wires 46 are drawn out of the sensor case 42 through the lead wire bundling cap 47. Some of the plurality of lead wires 46 are signal lines for transmitting detection signals of the sensor element to the analyzer 11b and the remaining lead wires 46 are power supply lines for supplying operation power to the sensor heater. The lead wires 46 are coated by a heat resistant and insulative Teflon (registered trademark) material.

Figure 5:
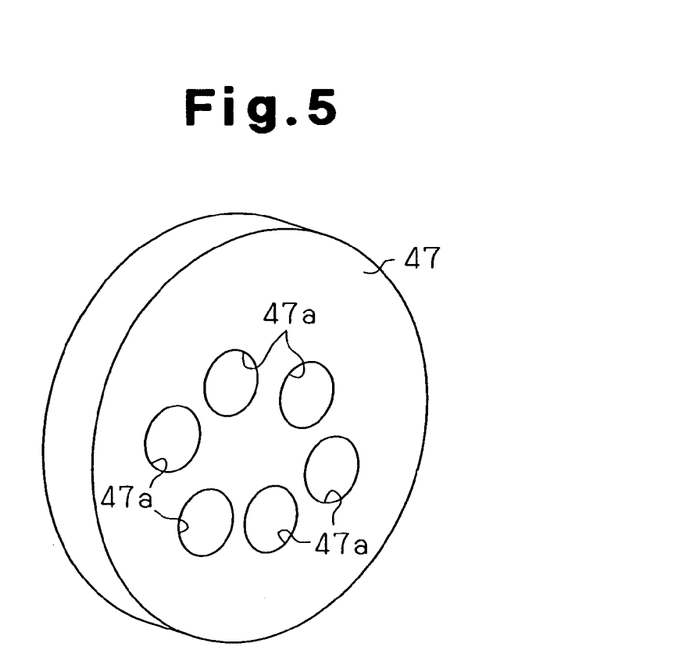
FIG. 5 is a perspective view showing a lead wire bundling cap included in the flue gas analyzer apparatus of FIG. 1.

As shown in FIG. 5, the lead wire bundling cap 47 is a circular plate having a plurality of lead wire holes 47a. The plurality of lead wire holes 47a are arranged annularly. The lead wire bundling cap 47 is made from an elastic, heat resistant, and insulative rubber material (such as fluorocarbon rubber or silicon rubber). The number of the lead wire holes 47a is the same as the number of the lead wires 46, and one lead wire 46 is inserted through one lead wire hole 47a. The bundle of the lead wires 46 drawn through the lead wire bundling cap 47 is inserted through a lead-wire insertion tube 48. A male connector 49 is connected to the ends of the lead wires 46.

A terminal box 51 will now be described.

Figure 3:
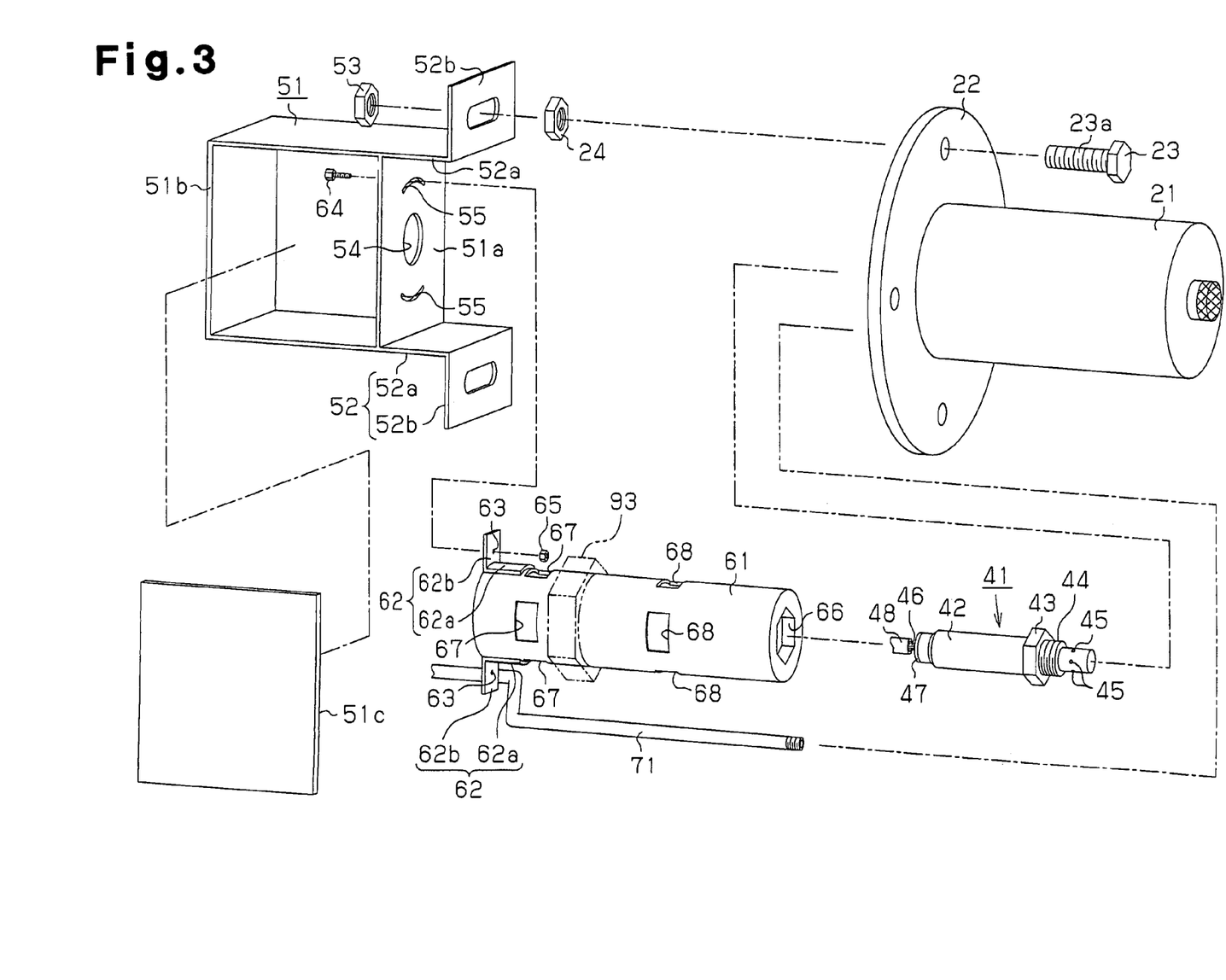
FIG. 3 is an exploded cross-sectional view of the flue gas analyzer apparatus of FIG. 1.

As shown in FIGS. 1 and 3, the transmitter 11a includes the terminal box 51. The terminal box 51 includes a side wall 51a located closer to the exhaust pipe 12 and a side wall 51b located farther from the exhaust pipe 12. The upper and lower bottom ends of the side wall 51a are welded and connected to two stays 52. Each stay 52 is L-shaped and includes a leg 52a and an attachment plate 52b. The leg 52a is fixed to the side wall 51a of the terminal box 51. The attachment plate 52b projects outward from the leg 52a. The attachment plate 52b of each stay 52 is fastened to the flange 14 of the exhaust pipe 12 by the bolt 23 and the nut 53.

As shown in FIG. 3, the side wall 51a of the terminal box 51 has a central hole 54 and two arcuate bolt holes 55 located at the outer side of the central hole 54. The bolt holes 55 are symmetric to each other about the central hole 54.

A tube joint 57 is fixed to the side wall 51b of the terminal box 51. An air supply tube 56, which is connected to the tube joint 57, extends through the central hole 54 and into the support tube 21 (more precisely, into the interior of a connector tube 61, which will be described later). The air supply tube 56 has an open end, or a nozzle 56a, which opens toward the basal portion of the gas sensor 41. The tube joint 57 is connected to a compressed air source (not shown), which generates cooling air. The cooling air is supplied through the air supply tube 56 toward the basal portion of the gas sensor 41. The length of the portion of the air supply tube 56 inserted into the connector tube 61 is determined so that the nozzle 56a is located at the basal side of the connector tube 61 with respect to the longitudinally middle position of the connector tube 61.

A cable joint 59 is fixed to the side wall 51b. An output cable 58, which is connected to the analyzer 11b, is inserted into the terminal box 51 through the cable joint 59. A female connector 60 is formed on an end of the output cable 58 in the terminal box 51. The female connector 60 is connected to the male connector 49 in the terminal box 51.

Figure 4:
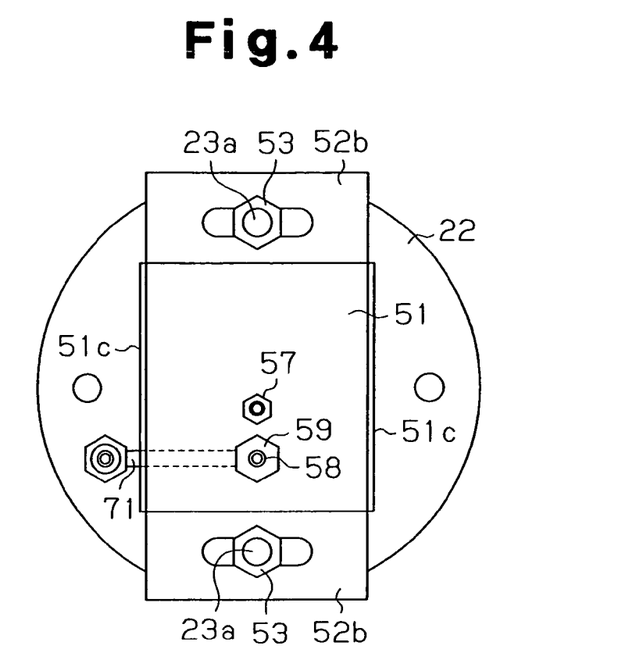
FIG. 4 is a plan view showing the flue gas analyzer apparatus of FIG. 1.

As shown in FIGS. 3 and 4, the terminal box 51 has two removable lids 51c (only one shown in FIG. 3) facing each other. A rectangular space is defined between the lids 51c and the side walls 51a and 51b. The terminal box 51 is opened by removing the lids 51c.

The connector tube 61 will now be described.

As shown in FIG. 1, the connector tube 61 is fixed to the outer surface of the side wall 51a of the terminal box 51. Two fixtures 62 are fixed, for example, through welding, to the outer circumferential surface of the basal portion of the connector tube 61 at opposite positions. Each fixture 62 is L-shaped and includes fastening pieces 62a and 62b. The fastening piece 62a is fixed to the outer surface of the connector tube 61. The fastening piece 62b is fixed to the side wall 51a of the terminal box 51. A bolt hole 63 is formed in each fastening piece 62b. As shown in FIG. 3, the bolt 64 is inserted through the bolt hole 55 of the side wall 51a of the terminal box 51 and the bolt hole 63 of the fastening piece 62b from inside the terminal box 51. A nut 65 is mated and fastened with the bolt 64. This connects the connector tube 61 to the terminal box 51.

Figure 2:
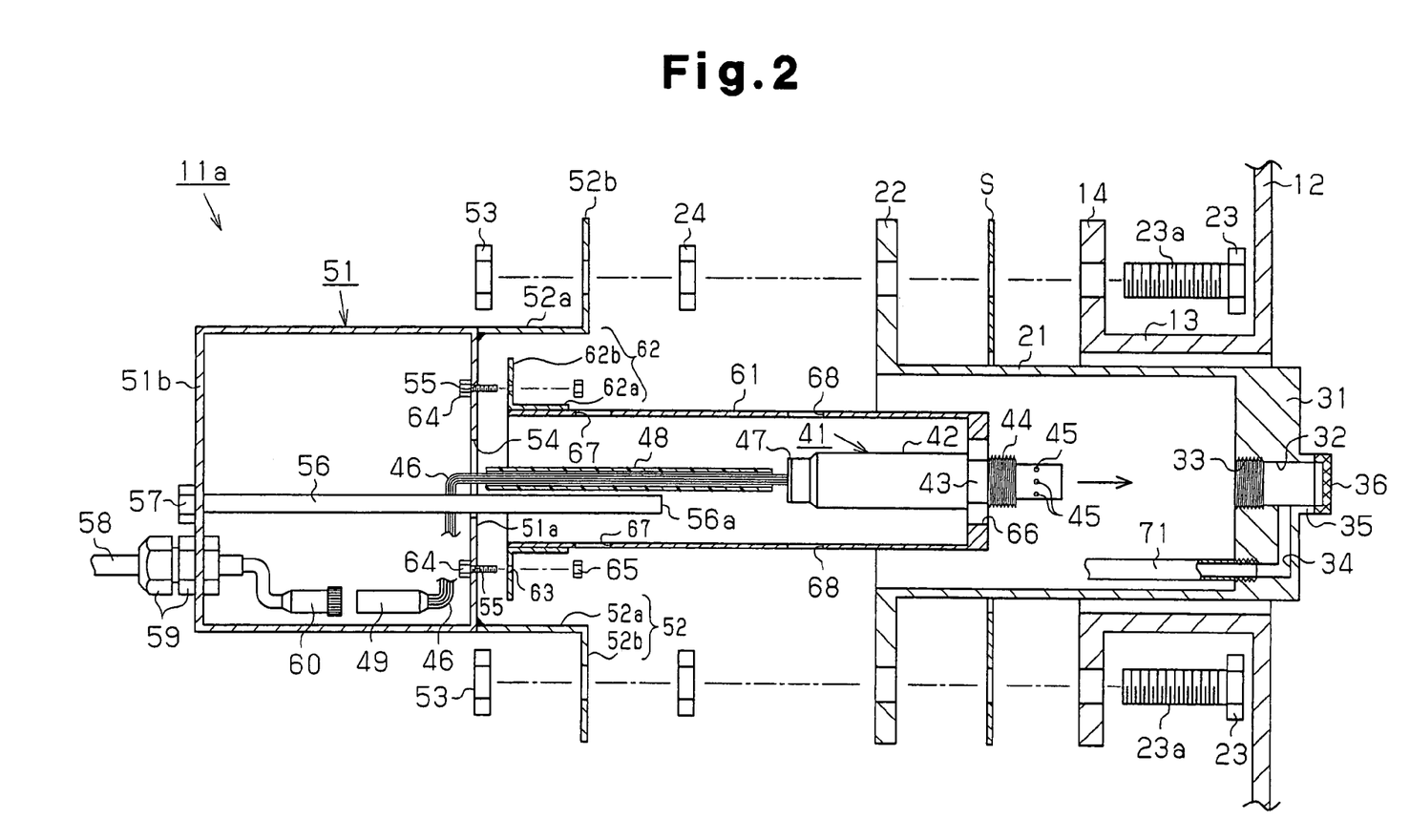
FIG. 2 is an exploded cross-sectional view of the flue gas analyzer apparatus of FIG. 1.

Referring to FIG. 1, the length of the connector tube 61 is determined so that the distal end wall of the connector tube 61 comes in contact with the distal end wall 31 in the support tube 21 when the terminal box 51 is fixed to the flange 14 of the reception tube 13. As shown in FIGS. 2 and 3, a hexagonal fitting hole 66 is formed in the distal end wall of the connector tube 61. The sensor nut 43 of the gas sensor 41 is fitted in the fitting hole 66. The basal portion of the sensor case 42 is accommodated in the connector tube 61 and the sensor nut 43 is fitted in the fitting hole 66 when the connector tube 61 is fixed to the side wall 51a of the terminal box 51 and the flange 22 of the support tube 21 and the attachment plate 52b of the terminal box 51 are fixed to the flange 14 of the reception tube 13.

As shown in FIGS. 1, 2, and 3, a plurality of air inlets 67 are formed in the basal portion of the connector tube 61. The air inlets 67 are formed at predetermined intervals in the circumferential direction of the connector tube 61. A plurality of air outlets 68 are formed at locations closer to the distal end of the connector tube 61 than the longitudinally middle position of the connector tube 61. The air outlets 68 are formed at predetermined intervals in the circumferential direction of the connector tube 61.

The locations of the air inlets 67 and the air outlets 68 will now be described. In the assembled state shown in FIG. 1, the air outlets 68 are located at positions corresponding to the basal portion of the gas sensor 41 (positions corresponding to the vicinity of the lead wire bundling cap 47). In other words, the air outlets 68 are located at positions closer to the exhaust pipe 12 than the flange 22 (positions inside the support tube 21). The air inlets 67 are located at positions farther from the exhaust pipe 12 than the flange 22 (positions outside the support tube 21).

As shown in FIG. 1, a correction gas supply tube 71 is arranged between the inner surface of the support tube 21 and the outer surface of the connector tube 61. The distal portion of the correction gas supply tube 71 is mated with the distal end wall 31 of the support tube 21 so that the interior of the correction gas supply tube 71 is connected to the connecting channel 34. Referring to FIG. 4, the correction gas supply tube 71 extends sideward in the terminal box 51 (toward the left as viewed in FIG. 4) in a space formed between the side wall 51a of the terminal box 51 and the flange 22 of the support tube 21. The basal portion of the correction gas supply tube 71 is connected to an external correction gas supply source (not shown). The correction gas is supplied from the correction gas supply source into the accommodation channel 32 via the correction gas supply tube 71 and the connecting channel 34.

In the first embodiment, the fitting hole 66 functions as a fitting structure. The fitting hole 66 and the sensor nut 43 function as an engagement structure. The lead wire bundling cap 47 functions as a basal portion of a gas sensor from which lead wires are drawn out to output sensor values. The air supply tube 56 functions as an air supply means.

The operation of the flue gas analyzer apparatus 11 of the first embodiment will now be described.

Gas sensor correction process will be described.

Before starting the measurement of the flue gas, a correction process of the gas sensor 41 is performed. First, a predetermined correction gas (e.g., an oxygen gas) is supplied from the correction gas supply source. The correction gas flows into the accommodation channel 32 via the correction gas supply tube 71 and the connecting channel 34. The correction gas then flows into the sensor case 42 via the gas inlets 45 and comes in contact with the sensor element accommodated in the sensor case 42. A predetermined voltage (electromotive force) that is in accordance with the correction gas is generated between two electrodes of the sensor element. A current signal that is in accordance with the voltage is generated. The current signal is transmitted to the analyzer 11b via the lead wires 46, the male connector 49, the female connector 60, and the output cable 58. The analyzer 11b stores the electric signal as a reference current. This completes the correction process of the gas sensor 41.

Flue gas introduction process will now be described.

After the correction process is completed, the transmitter 11a is inserted into the reception tube 13 and is fixed to the exhaust pipe 12. The distal end (filter 36) of the fixed transmitter 11a is exposed in the flue. The flue gas that flows in the exhaust pipe 12 flows into the accommodation channel 32 through the distal end surface and outer circumferential surface of the filter 36. In this way, the flue gas is drawn through the filter 36 in various directions. This enables a sufficiently large amount of flue gas to be drawn into the accommodation channel 32. The flue gas that has flowed into the accommodation channel 32 flows into the sensor case 42 via the gas inlets 45. The flue gas that has flowed into the sensor case 42 comes into contact with the sensor element accommodated in the sensor case 42. Voltage (electromotive force) that is in accordance with the concentration of a predetermined chemical component (e.g., a nitrogen oxide) contained in the flue gas is generated between the two electrodes of the sensor element to generate an actual current signal that is in accordance with the electromotive force. The actual current signal is transmitted to the analyzer 11b via the lead wires 46, the male connector 49, the female connector 60, and the output cable 58. The analyzer 11b compares the actual current signal with the reference signal and calculates the concentration of the predetermined chemical component in the flue gas based on the deviation of the actual current signal from the reference signal.

The cooling air supply process will now be described.

During analysis of the flue gas, the cooling air is supplied to the connector tube 61 through the tube joint 57 and the air supply tube 56. The nozzle 56a of the air supply tube 56 ejects the cooling air toward the basal portion of the gas sensor 41. The flow of the cooling air is guided along the inner surface of the connector tube 61 so that it reaches the vicinity of the basal portion of the gas sensor 41. The connector tube 61 guides the cooling air so that it flows toward the basal end of the gas sensor 41 without diffusing and efficiently cools the basal portion of the gas sensor 41.

The cooling air ejected from the nozzle 56a produces an airflow. In detail, the cooling air ejected from the nozzle 56a flows along the inner surface of the connector tube 61 toward the distal end of the connector tube 61 and flows out of the connector tube 61 through the air outlets 68. The cooling air then flows along the inner surface of the support tube 21 toward the flange 22 and flows out from a gap formed between the flange 22 and the attachment plate 52b (terminal box 51). The cooling air that flows in the connector tube 61 lowers the internal pressure at the basal portion of the connector tube 61. The lowered pressure causes air outside the flange 22 of the support tube 21 to flow into the connector tube 61 via the air inlets 67. This air flows toward the distal end of the connector tube 61 together with the cooling air (this phenomenon is referred to as the so-called ejector effect). Such airflow prevents eddy from being produced in the connector tube 61 (particularly at the inner surface of the connector tube 61) and enables smooth airflow in the connector tube 61. As a result, the cooling air is efficiently supplied to the basal portion of the gas sensor 41.

The efficient supply of cooling air efficiently cools the lead wire bundling cap 47 attached to the basal portion of the gas sensor 41. Thus, the lead wires 46 are efficiently cooled. That is, the smooth flow of the cooling air efficiently removes heat from the lead wire bundling cap 47 and the lead wires 46. As a result, the temperature of the lead wire bundling cap 47 and the lead wires 46 is prevented from increasing, and heat damage of the lead wire bundling cap 47 and the lead wires 46 is avoided.

After heat exchange with the lead wire bundling cap 47 and the lead wires 46, the cooling air flows out of the connector tube 61 via the air outlets 68. The air outlets 68 are formed at positions corresponding to the lead wire bundling cap 47. Thus, the body (sensor case 42) of the gas sensor 41 is not forcibly or actively cooled by the flow of the cooling air.

A procedure for replacing the gas sensor 41 will now be described. First, the gas sensor 41 is removed from the support tube 21. In detail, the lids 51c of the terminal box 51 are removed, and the male connector 49 and the female connector 60 in the terminal box 51 are disconnected from each other. The bolts 64 and the nuts 65 are removed to release the terminal box 51 from the connector tube 61. The bolts 23 and the nuts 53 are also removed to release the terminal box 51 from the flange 22 of the support tube 21. While holding the terminal box 51, the lead wires 46 connected to the male connector 49 are pulled out of the central hole 54 of the terminal box 51. The connector tube 61 is rotated in a predetermined direction. The rotation of the connector tube 61 is transmitted to the gas sensor 41 through the fitting hole 66 and the sensor nut 43 so that the connector tube 61 and the gas sensor 41 rotate integrally. When the threaded female portion 33 is disengaged from the threaded male portion 44, the gas sensor 41 becomes removable. In a state in which the gas sensor 41 is fitted in the fitting hole 66 of the connector tube 61, the connector tube 61 is pulled out of the support tube 21. After that, the gas sensor 41 is removed from the connector tube 61. When pulling the gas sensor 41 out of the accommodation channel 32 of the distal end wall 31, the filter 36 prevents hot air in the flue from flowing into the support tube 21 through the accommodation channel 32. This completes the removal of the gas sensor 41.

Next, the attachment of the gas sensor 41 to the support tube 21 will be described. To attach a gas sensor 41 to the support tube 21, the gas sensor 41 is first connected to the distal end of the connector tube 61. More specifically, the sensor nut 43 is fitted in the fitting hole 66, the connector tube 61 is inserted into the basal end opening of the support tube 21, and the distal end of the gas sensor 41 is inserted into the accommodation channel 32 of the distal end wall 31. The connector tube 61 is then rotated in the direction opposite the direction it is rotated when removing the gas sensor 41 from the support tube 21. The rotation of the connector tube 61 is transmitted to the gas sensor 41 via the fitting hole 66 and the sensor nut 43. As a result, the connector tube 61 and the gas sensor 41 rotate integrally. The gas sensor 41 moves in the distal direction when fastening the threaded male portion 44 and the threaded female portion 33. The movement of the gas sensor 41 in the distal direction is restricted as the sensor nut 43 comes into contact with the inner surface of the distal end wall 31 of the support tube 21.

Next, the lead wires 46 connected to the male connector 49 are inserted through the central hole 54 of the terminal box 51. The bolts 64 and the nuts 65 are mated to fix the terminal box 51 to the connector tube 61. Next, the bolts 23 and the nuts 53 are mated to fix the terminal box 51 to the flange 22 of the support tube 21. Finally, the male connector 49 and the female connector 60 are connected to each other in the terminal box 51, and the lids 51c are attached to the terminal box 51. This completes the replacement of the gas sensor 41.

During the replacement of the gas sensor 41, the connector tube 61 functions as a jig for releasing the gas sensor 41 from the support tube 21 and as a jig for fixing the gas sensor 41 to the support tube 21. This structure eliminates the need for a special jig for releasing the gas sensor 41 from the support tube 21.

The first embodiment has the advantages described below.

(1) The distal opening of the air supply tube 56 arranged in the connector tube 61 faces toward the basal portion of the gas sensor 41. The flow of the cooling air ejected from the distal opening reaches at least the basal portion of the gas sensor 41 and cools the lead wires 46 and the lead wire bundling cap 47, which is attached to the basal portion of the gas sensor 41. As a result, the temperature of the lead wire bundling cap 47 and the lead wires 46 is prevented from increasing, and heat damage of the lead wire bundling cap 47 and the lead wires 46 is avoided. Rubber material may be used for the lead wire bundling cap 47. Thus, an expensive material having high heat resistance does not need to be used for the lead wire bundling cap 47. This prevents the component costs of the flue gas analyzer apparatus 11 from increasing.

(2) The cooling air flows in the connector tube 61 toward the basal portion of the gas sensor 41. The cooling air is guided by the connector tube 61 without diffusing as it flows toward the basal portion of the gas sensor 41. This effectively cools the basal portion of the gas sensor 41.

(3) The nozzle 56a of the air supply tube 56 generates a flow of cooling air toward the basal portion of the gas sensor 41. The flow of cooling air, which is efficiently supplied to the basal portion of the gas sensor 41, effectively cools the lead wire bundling cap 47 and the lead wires 46.

(4) The distal portion of the gas sensor 41 is mated with the distal end wall 31 of the support tube 21. The connector tube 61 is long enough to accommodate most of the gas sensor 41. The gas sensor 41 has an outer surface on which the sensor nut 43 is formed. The connector tube 61 has a distal end in which the fitting hole 66 is formed. The sensor nut 43 is fitted in the fitting hole 66. Accordingly, when the connector tube 61 is rotated, the gas sensor 41 rotates integrally with the connector tube 61. For example, the gas sensor 41 may be removed from the support tube 21 by rotating the connector tube 61 in a predetermined direction and be attached to the support tube 21 by rotating the connector tube 61 in the direction opposite to the predetermined direction. The connector tube 61 functions as a jig for attaching and removing the gas sensor 41 to and from the support tube 21. This eliminates the need for a special jig. The relatively simple structure including the sensor nut 43 and the fitting hole 66 improves efficiency for removing and attaching the gas sensor 41. Thus, the flue gas analyzer apparatus 11 does not have a complex structure.

(5) The air inlets 67 are formed in the basal end of the connector tube 61. The ejector effect caused by the cooling air flowing from the basal end of the connector tube 61 to the distal end of the connector tube 61 enables ambient air to be drawn into the connector tube 61 through the air inlets 67. The ambient air then flows toward the distal end of the connector tube 61. Such airflow generated by the ejector effect prevents the generation of eddies in the connector tube 61. The cooling air and the outside air flow smoothly in the connector tube 61. As a result, the cooling air is efficiently supplied to the basal portion of the gas sensor 41. Accordingly, the basal portion of the gas sensor 41 (more specifically, the lead wire bundling cap 47 and the lead wires 46) is efficiently cooled.

(6) The plurality of air outlets 68 are formed in the connector tube 61 at locations corresponding to the basal portion of the gas sensor 41 (that is, locations corresponding to the lead wire bundling cap 47). The cooling air cools the vicinity of the basal portion of the gas sensor 41 and flows out of the connector tube 61 through the air outlets 68. The flow of the cooling air does not actively cool the body (sensor case 42) of the gas sensor 41. It is preferable that the sensor element included in the gas sensor 41 not be cooled. Accordingly, the sensor element is heated by the sensor heater and maintained at a predetermined temperature. This enables the sensor element to detect a predetermined chemical component with high accuracy.

(7) The lead wires 46 are drawn from the gas sensor 41 through the lead wire bundling cap 47 into the connector tube 61 and then out of the connector tube 61. Thus, in the connector tube 61, the lead wires 46 are cooled by the flow of the cooling air.

(8) The nozzle 56a of the air supply tube 56 is located at a position slightly closer to the basal end of the connector tube 61 than the longitudinally middle position of the connector tube 61. This arrangement enables the cooling air to efficiently and uniformly cool the basal portion of the gas sensor 41 (lead wire bundling cap 47) and the lead wires 46 that extend from the basal portion of the gas sensor 41. For example, if the nozzle 56a is located too close to the basal portion of the gas sensor 41, the lead wire bundling cap 47 may be sufficiently cooled. However, the lead wires 46 may not be sufficiently cooled. If the nozzle 56a is located too far from the basal portion of the gas sensor 41, the lead wires 46 may be sufficiently cooled. However, the lead wire bundling cap 47 may not be sufficiently cooled.

(9) The filter 36, which is cup-shaped, is fixed to the distal end of the support tube 21. The distal end surface and the outer circumferential surface of the filter 36 are exposed in the flue. The flue gas in the exhaust pipe 12 is drawn through the filter 36 in various directions. More specifically, the flue gas flows through the distal end surface and the outer circumferential surface of the filter 36. This enables a sufficiently large amount of flue gas to reach the sensor element accommodated in the sensor case 42. This improves the response characteristic of the sensor element.

Figure 6A:
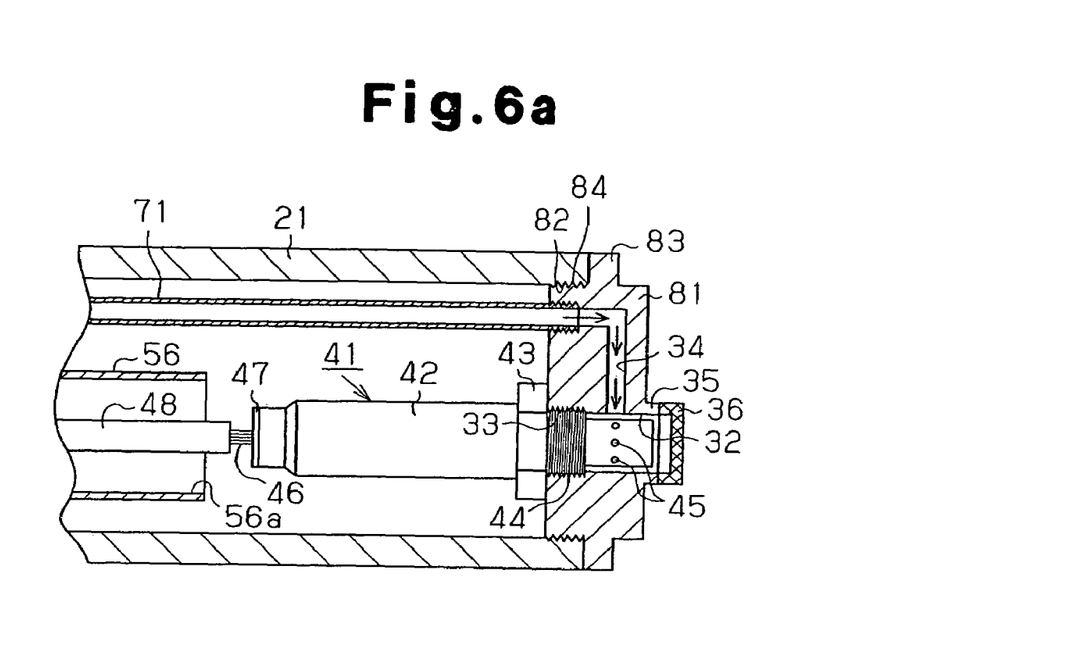
FIG. 6a is a partial cross-sectional view of a flue gas analyzer apparatus according to a second embodiment of the present invention.
Figure 6B:
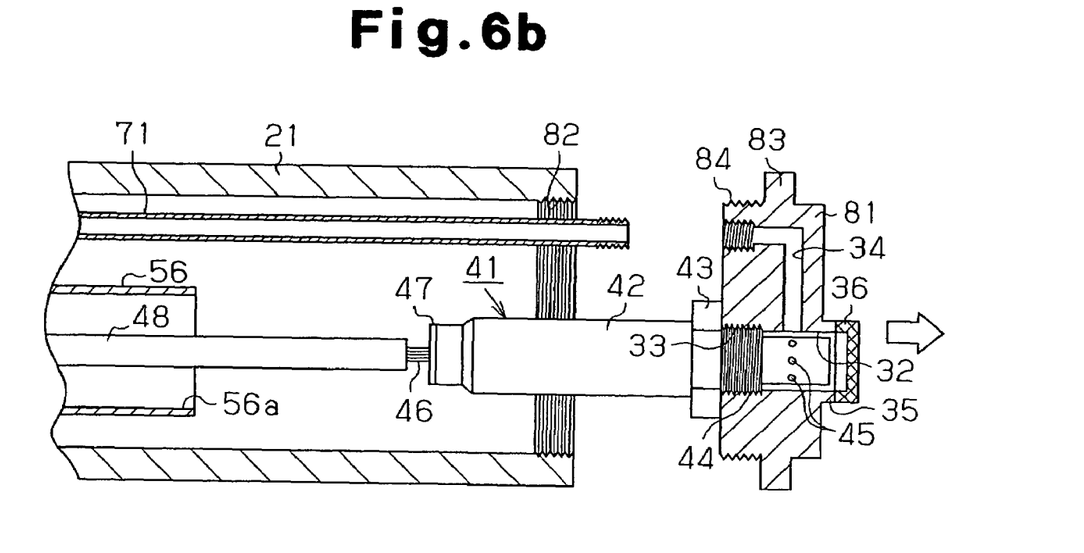
FIG. 6b is an exploded cross-sectional view of the same flue gas analyzer apparatus.

A flue gas analyzer apparatus 11 according to a second embodiment of the present invention will now be described focusing on differences from the first embodiment. The second embodiment differs from the first embodiment mainly in its structure for mounting a gas sensor.

In the second embodiment, a support tube 21 has a distal end opening to which a removable adaptor plug 81 is attached as shown in FIG. 6a. A threaded female portion 82 is formed in the inner surface of the support tube 21 near the distal end. The adaptor plug 81 has a circumferential surface on which a threaded male portion 84 and a flange 83 are formed. The threaded male portion 84 of the adaptor plug 81 and the threaded female portion 82 of the support tube 21 are mated together so that the adaptor plug 81 is fixed to the support tube 21. The adaptor plug 81 has the same structure as the structure of the distal end wall 31 of the support tube 21 in the first embodiment. More specifically, the adaptor plug 81 has an accommodation channel 32, a connecting channel 34, a filter support projection 35, and a filter 36. The distal end of the gas sensor 41 is accommodated in the accommodation channel 32 when the gas sensor 41 is attached to the adaptor plug 81.

The flue gas analyzer apparatus 11 of the second embodiment does not include the connector tube 61 of the first embodiment. In the second embodiment, an air supply tube 56 is used in lieu of the connector tube 61 to cover the lead wires 46 and the lead-wire insertion tube 48. The fixtures 62 (refer to FIG. 3) are fixed to the basal end of the air supply tube 56 through, for example, welding. The air supply tube 56 is fastened to the side wall 51a of the terminal box 51 by the bolts 64 and nuts 65 with the fixtures 62. The length of the air supply tube 56 is determined so that the nozzle 56a (distal end opening) of the air supply tube 56 is located near the basal portion of the gas sensor 41 (more precisely, a lead wire bundling cap 47) but does not come into contact with the basal portion of the gas sensor 41.

Cooling air generated by a compressed air source is supplied into the terminal box 51 through the tube joint 57.

The cooling air flows into the basal portion of the air supply tube 56 through the central hole 54 of the terminal box 51. The cooling air then flows out of the air supply tube 56 through the nozzle 56a and flows towards the basal portion of the gas sensor 41. The nozzle 56a of the air supply tube 56 opens toward the basal portion of the gas sensor 41. Thus, the cooling air flows toward the basal portion of the gas sensor 41 and efficiently cools the basal portion of the gas sensor 41.

The replacement procedure for the gas sensor 41 will now be described. To remove the gas sensor 41, the lids 51c of the terminal box 51 are first removed as shown in FIG. 3. Next, the male connector 49 and the female connector 60 in the terminal box 51 are disconnected from each other as shown in the state of FIG. 2. The nuts 53 are removed to release the terminal box 51 from the flange 22 of the support tube 21. While holding the terminal box 51, the male connector 49 and the lead wires 46 are pulled out of the central hole 54 of the terminal box 51. The bolts 23 and the nuts 24 are removed to release the flange 22 of the support tube 21 from the flange 14 of the reception tube 13. The support tube 21 is pulled out of the reception tube 13, and the correction gas supply tube 71 is disconnected from the support tube 21 as shown in the state of FIG. 6b.

Referring to FIG. 6b, the adaptor plug 81 is rotated in a predetermined direction to remove the adaptor plug 81 from the distal portion of the support tube 21. The gas sensor 41 is pulled out of the support tube 21 together with the adaptor plug 81 (as indicated by the arrow in FIG. 6b). As a result, the lead wires 46, the lead-wire insertion tube 48, and the male connector 49 are also pulled out of the support tube 21. Finally, the gas sensor 41 is rotated in a predetermined direction to disconnect the gas sensor 41 from the adaptor plug 81. This completes the removal of the gas sensor 41.

Next, the attachment of the gas sensor 41 will be described. First, a gas sensor 41 for replacement is fixed to the adaptor plug 81. The male connector 49, the lead-wire insertion tube 48, and the lead wires 46 are inserted into the distal end opening of the support tube 21. Then, the adaptor plug 81 to which the gas sensor 41 is fixed is mated with the distal end opening of the support tube 21. Movement of the adaptor plug 81 in the inward direction (to the left as viewed in FIG. 6b) is restricted when the flange 83 of the adaptor plug 81 comes into contact with the end surface around the distal end opening of the support tube 21. Then, the support tube 21 to which the gas sensor 41 is fixed is inserted in the reception tube 13. Next, the correction gas supply tube 71 is inserted into the basal end opening of the support tube 21, and the distal portion of the correction gas supply tube 71 is connected to the connecting channel 34, which is formed in the adaptor plug 81. Subsequently, the operations for removing the gas sensor 41 are performed in a reversed order. This completes the attachment of the gas sensor 41.

The second embodiment has the advantages described below.

(10) The gas sensor 41 is attached to the removable adaptor plug 81, which is fixed to the distal end of the support tube 21. The adaptor plug 81 is removed from the support tube 21 to remove the gas sensor 41 from the support tube 21. Thus, a special jig for attaching or removing the gas sensor 41 to or from the support tube 21 is not necessary. Further, the replacement procedure for the gas sensor 41 is simple.

(11) The distal end opening of the air supply tube 56 opens toward the basal portion of the gas sensor 41. Thus, the cooling air is supplied at least to the basal portion of the gas sensor 41. The cooling air cools the lead wire bundling cap 47 and the lead wires 46 in the air supply tube 56. As a result, the temperature of the lead wire bundling cap 47 and the lead wires 46 is prevented from increasing, and heat damage of the lead wire bundling cap 47 and the lead wires 46 is avoided. A rubber material may be used for the lead wire bundling cap 47, and an expensive material having high heat resistance does not need to be used for the lead wire bundling cap 47. This prevents the component costs of the flue gas analyzer apparatus 11 from increasing.

(12) The cooling air drawn into the basal side of the air supply tube 56 flows into the air supply tube 56 and is guided to the vicinity of the basal portion of the gas sensor 41 without diffusing. As a result, the cooling air effectively cools the basal portion of the gas sensor 41.

A flue gas analyzer apparatus 11 according to a third embodiment of the present invention will now be described with reference to FIGS. 7 to 10. The third embodiment is described focusing on differences from the second embodiment. The flue gas analyzer apparatus 11 of the third embodiment includes an adaptor plug 81 to which a gas sensor 41 is attached. The adaptor plug 81 includes a filter support projection 35. A filter 36, which is a circular plate, is fitted to the end surface of the filter support projection 35. A filter cover 85 having a central hole 85a is mated with the filter 36. The filter 36 is exposed through the central hole 85a of the filter cover 85. The central hole 85a functions as an inlet for drawing in gas to be measured. A packing 86 is arranged between a flange 83 of the adaptor plug 81 and an end face of the support tube 21. The packing 86 ensures hermetic sealing of the support tube 21.

Figure 9:
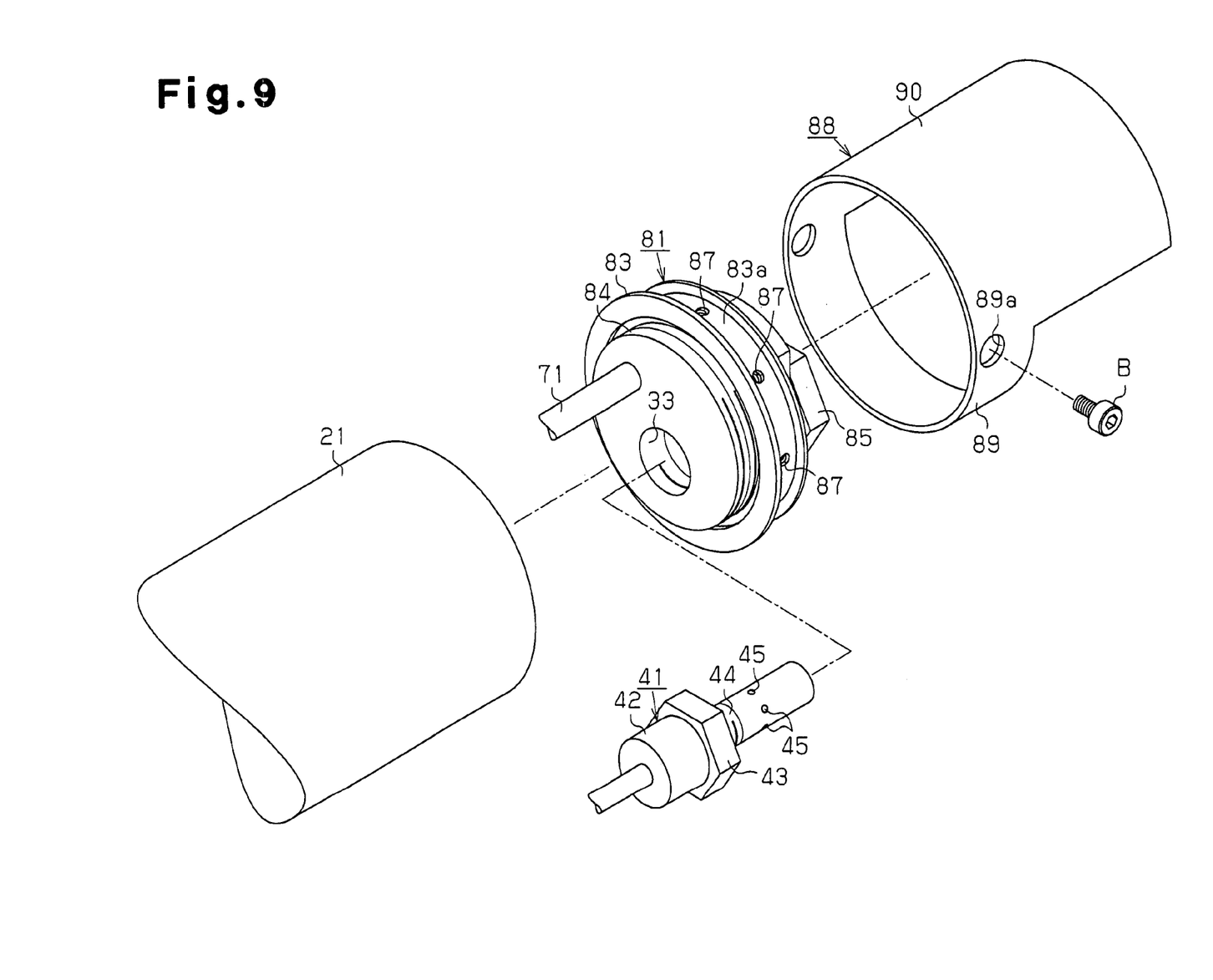
FIG. 9 is an exploded perspective view showing an adaptor plug and a protective cap of FIG. 7.
Figure 10:
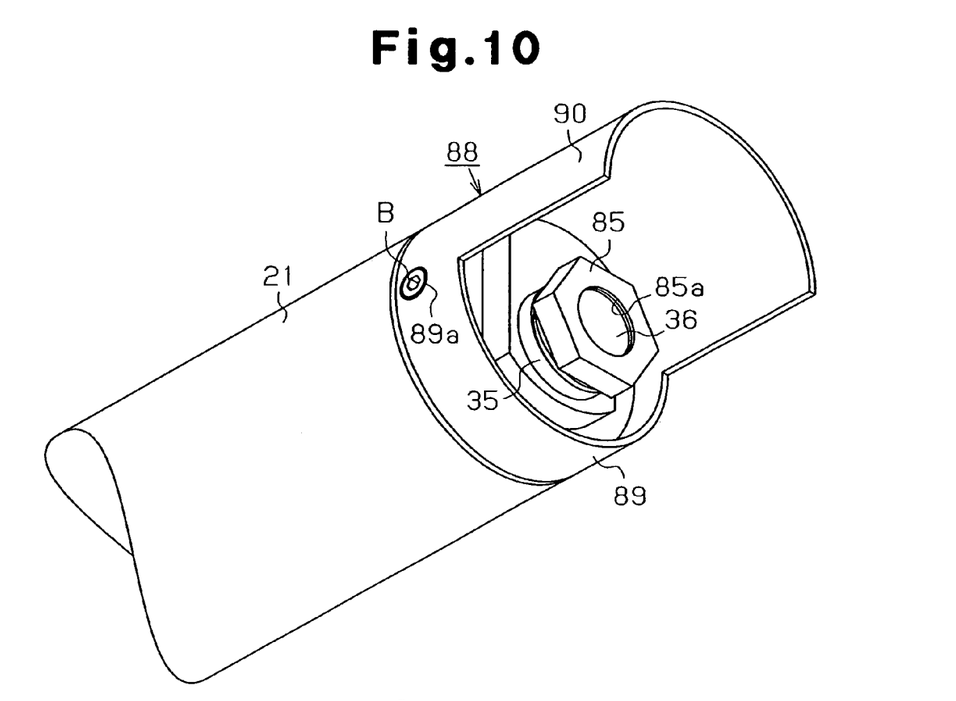
FIG. 10 is a partial perspective view showing the flue gas analyzer apparatus of FIG. 7.

As shown in FIG. 9, an annular groove 83a is formed in the flange 83 of the adaptor plug 81. A plurality of (eight in the third embodiment) threaded female portions 87 are formed in the groove 83a of the flange 83. The threaded female portions 87 are arranged at fixed intervals in the circumferential direction of the flange 83 and open in the groove 83a. The threaded female portions 87 are formed by a plurality pairs of threaded female portions 87. In the example shown in FIG. 9, the eight threaded female portions 87 are formed by four pairs of threaded female portions 87 arranged so that two threaded female portions 87 in each pair are opposed to each other with respect to the center axis of the adaptor plug 81.

Figure 8:
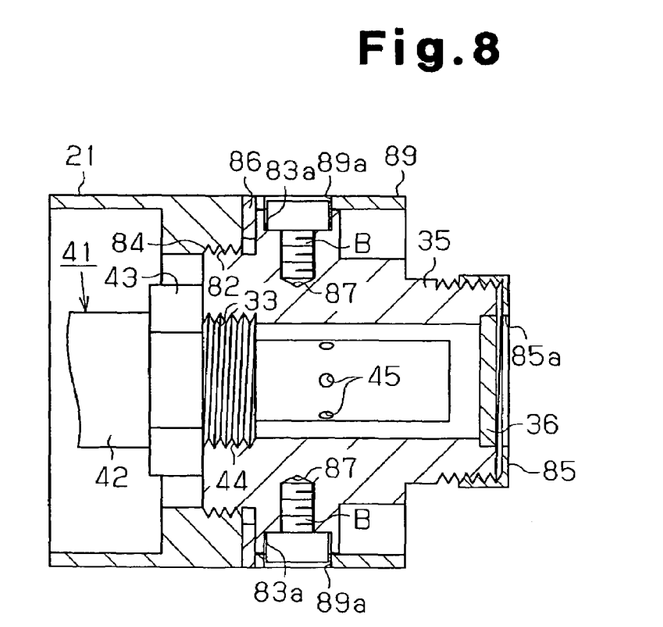
FIG. 8 is a cross-sectional view of the flue gas analyzer apparatus taken along line 8-8 in FIG. 7.

A protective cap 88 is attached to the adaptor plug 81. The protective cap 88 includes an annular socket 89 and a semi-cylindrical shield wall 90. The inner diameter of the socket 89 is substantially the same as or slightly greater than the outer diameter of the flange 83. As shown in FIG. 8, two engagement holes 89a are formed on the socket 89 at opposite positions.

The socket 89 is fitted to the flange 83 of the adaptor plug 81 in a manner that the a pair of engagement holes 89a are aligned with one of the pairs of threaded female portions 87 that are formed in the flange 83. A bolt B is inserted from the outer side of the socket 89 into each engagement hole 89a. Each bolt B is mated with the corresponding threaded female portion 87. This fixes the protective cap 88 to the adaptor plug 81. As shown in FIG. 8, each bolt B, which is mated with the threaded female portion 87, is received by the threaded female portion 87 and the engagement hole 89a. In particular, the head of the bolt B is engaged in the engagement hole 89a of the socket 89. The engagement of the bolt B prevents the protective cap 88 from rotating with respect to the adaptor plug 81 and being separated from the adaptor plug 81.

Figure 7:
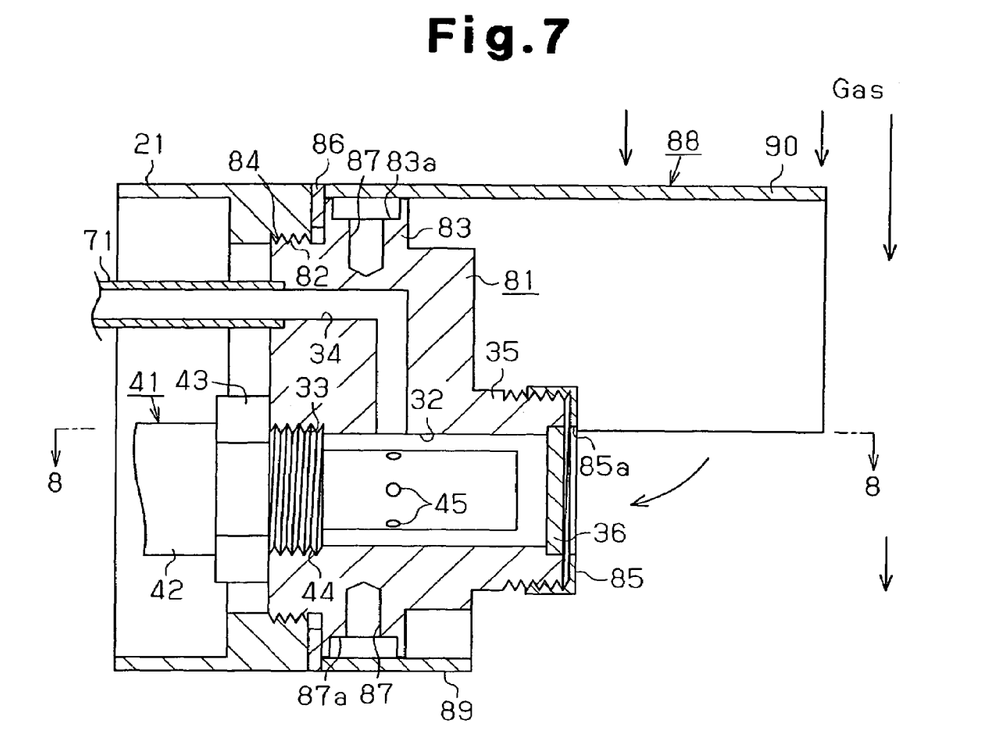
FIG. 7 is a partial cross-sectional view of a flue gas analyzer apparatus according to a third embodiment of the present invention.

When the protective cap 88 is attached to the adaptor plug 81, the distal end of the shield wall 90 extends further from the filter support projection 35. In this state, the shield wall 90 is located upstream of the filter support projection 35 with respect to the flow of the gas to be measured. The bolts B do not project from the outer surface of the socket 89.

In the third embodiment, the adaptor plug 81 functions as a sensor attachment member. The threaded female portion 82 functions as an opening formed at a distal portion of a support tube. Each threaded female portion 87 functions as an attachment unit. Each bolt B functions as an engagement body. The bolts B and the socket 89 function as an engagement structure.

The third embodiment has the advantages described below.

(13) The adaptor plug 81 has the measurement gas inlet (central hole 85a) for drawing in the gas to be measured that flows through the exhaust pipe 12. The shield wall 90 is arranged upstream to the filter support projection 35 with respect to the flow of the measurement gas. The shield wall 90 blocks the flow of the measurement gas. The measurement gas that passes the shield wall 90 flows slowly into the central hole 85a. As a result, the gas sensor 41 analyzes the measurement gas of which flow has been weakened. In this way, the shield wall 90 prevents the gas sensor 41 from being affected by a strong flow of measurement gas. This enables stable analysis of the measurement gas.

(14) The flow of the measurement gas is blocked by the shield wall 90. The measurement gas that passes the shield wall 90 flows slowly into the central hole 85a. This prevents the filter 36 from being clogged with dust that flows through the exhaust pipe 12.

(15) The protective cap 88 including the shield wall 90 is removable from the adaptor plug 81. Thus, the protective cap 88 may be removed in accordance with the force of the flow of the measurement gas. For example, when the flow of the measurement gas is strong, the protective cap 88 may be attached to the adaptor plug 81 to weaken the flow of the measurement gas with the shield wall 90. When the flow of the measurement gas is mild, the protective cap 88 may be removed. In this way, the force of the flow of the measurement gas drawn into the central hole 85a may be adjusted.

(16) The engagement structure including the adaptor plug 81 and the socket 89 enables the protective cap 88 to be attached to the adaptor plug 81. The engagement structure includes the fitting of the flange 83 of the adaptor plug 81 into the socket 89 and the engagement of the two engagement holes 89a formed in the socket 89 and the bolts B. The shield wall 90 is only required to function to have the flow of the measurement gas in the flue blocked or detoured. Thus, the shield wall 90 does not have to be completely fixed to the adaptor plug 81 as long as it can be separated from the adaptor plug 81. Thus, the shield wall 90. The engagement between the engagement holes 89a of the socket 89 and the bolts B is sufficient for detachably supporting the protective cap 88 with the adaptor plug 81. This engagement is realized simply by attaching the protective cap 88 to the adaptor plug 81 and tightening the bolts B. Thus, the structure for attaching the protective cap 88 to the adaptor plug 81 is simple.

(17) The threaded female portions 87 are formed on the flange 83 of the adaptor plug 81 at predetermined intervals. The two engagement holes 89a of the protective cap 88 are aligned with one of the pairs of threaded female portions 87 so that the shield wall 90 is arranged upstream in the flow of the measurement gas.

(18) The bolts B do not project from the outer surface of the socket 89. No projections are formed on the outer surface of the support tube 21 and the protective cap 88. Thus, the flue gas analyzer apparatus 11 has a satisfactory appearance. Further, the support tube 21 is smoothly inserted in the reception tube 13. Thus, the transmitter 11a is easily attached to the exhaust pipe 12. If the bolts B project from the outer surface of the socket 89, the projected bolts B may abut against the reception tube 13 and obstruct insertion of the support tube 21 into the reception tube 13. Further, the support tube 21 may require accurate positioning inserting the support tube 21 into the reception tube 13 so that the projected bolts B do not abut against the reception tube 13. Projection of the bolts B would lower efficiency when attaching the transmitter 11a to the exhaust pipe 12. This becomes more outstanding as the gap between the inner surface of the reception tube 13 and the outer surface of the support tube 21 decreases.

(19) The filter 36 and the filter cover 85 are attached to the filter support projection 35 of the adaptor plug 81. The filter cover 85 is removable. Thus, the attachment, replacement, and cleaning of the filter 36 is easy.

It should be apparent to those skilled in the art that the present invention may be embodied in many other specific forms without departing from the spirit or scope of the invention. Particularly, it should be understood that the present invention may be embodied in the following forms.

Figure 11:
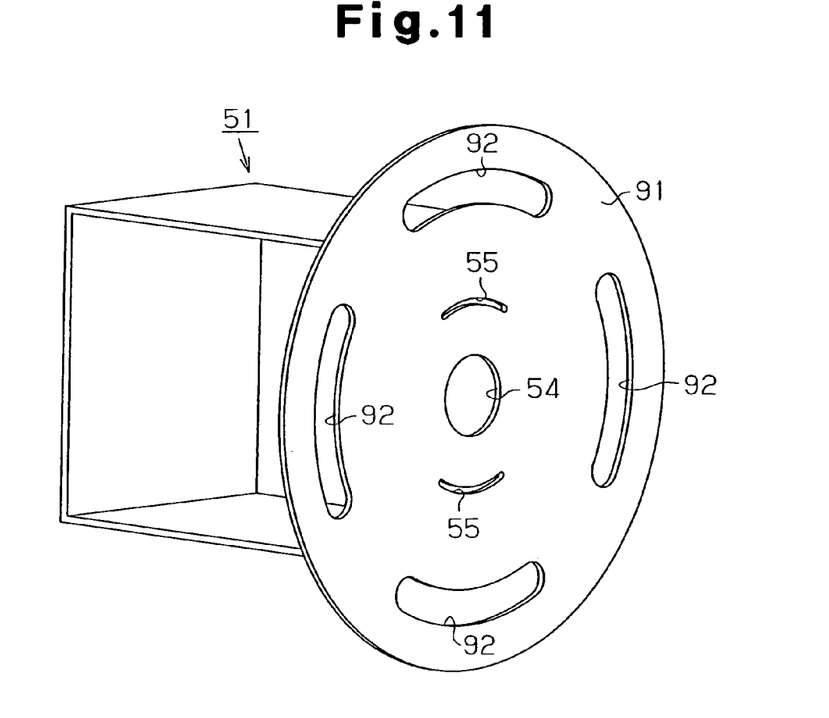
FIG. 11 is a perspective view showing a modification of a terminal box.

As shown in FIG. 11, the side wall 51a of the terminal box 51 in the first and second embodiments may be changed to a circular-plate fastening member 91. In this case, a central hole 54 and bolt holes 55 are formed in the fastening member 91. A plurality of-bolt holes 92 are formed around the central hole 54 and the bolt holes 55. The bolt holes 92 are formed at predetermined intervals in the circumferential direction of the fastening member 91. Each bolt hole 92 extends in the circumferential direction of the fastening member 91. This structure eliminates the need for the stays 52 and reduces the number of parts of the flue gas analyzer apparatus 11.

In the first embodiment, a hexagonal nut 93 (as shown by broken lines in FIG. 3) may be arranged on the outer surface of the connector tube 61. The connector tube 61 is rotated while holding the hexagonal nut 93. This facilitates the removal and attachment of the connector tube 61.

In the first embodiment, the gas sensor 41 is entirely covered by the connector tube 61 in the support tube 21. However, part of the gas sensor 41 (at least its basal portion) may be accommodated in the connector tube 61. An engagement structure may be formed on the inner surface of the connector tube 61 and the outer surface of the gas sensor 41 that face each other. The fitting hole 66 may be formed in the inner surface of the connector tube 61, and the sensor nut 43 may be formed on the outer surface of the gas sensor 41. The fitting hole 66 does not have to be formed on the distal end of the connector tube 61. For example, the fitting hole 66 may be formed on the body of the connector tube 61.

In the first embodiment, the nozzle 56a of the air supply tube 56 is located at a position slightly closer to the basal end of the connector tube 61 than the longitudinally middle position of the connector tube 61. However, the location of the nozzle 56a may be changed by adjusting the length of the connector tube 61. For example, the nozzle 56a may be located at the middle position of the connector tube 61 or at a position closer to the distal end of the connector tube 61 by increasing the length of the air supply tube 56. The nozzle 56a may be arranged at a position closer to the basal end of the connector tube 61 than the middle position of the connector tube 61 by decreasing the length of the air supply tube 56. Instead of arranging the air supply tube 56 in the connector tube 61, cooling air may be supplied into the terminal box 51. In this case, the air supplied to the terminal box 51 flows into the connector tube 61 and toward the basal portion of the gas sensor 41.

In the first embodiment, there may be only one air inlet 67.

In the first embodiment, there may be only one air outlet 68.

In the first embodiment, each air inlet 67 is formed in alignment with a corresponding air outlet 68 (refer to FIG. 3). However, each air inlet 67 may be formed out of alignment with the corresponding air outlet 68. For example, the air inlets 67 may be formed at positions shifted from the positions of the corresponding air outlets 68 by 90 degrees in the circumferential direction of the connector tube 61. This structure cools the basal portion (lead wire bundling cap 47) of the gas sensor 41 and the lead wires 46 more efficiently.

In the third embodiment, the number of engagement holes 89a of the socket 89 should not be limited to only two. The socket 89 may have one engagement hole 89a or three or more engagement holes 89a.

In the third embodiment, the bolts B may be changed to other engagement bodies such as pins, and the threaded female portions 87 may be changed to simple holes. In such a case, the pins and the socket 89 form the engagement structure.

The plurality of lead wires 46 may be electric wires coated with heat-resistant fibers. For example, electric wires coated with glass fibers or ceramic electric wires made of pure nickel may be used as the lead wires 46.

The lead wire bundling cap 47 is formed from elastic, heat resistant, and insulative materials, such as fluorocarbon rubber and silicon rubber. The lead wire bundling cap 47 may also be formed from heat resistant, insulative, high temperature fire-proof fibers, such as ceramic fibers and glass fibers. The lead wire bundling cap 47 may be formed from machinable ceramics (mica).

In the first embodiment, a wall that is the same as the shield wall 90 of the third embodiment may be fixed to the distal end wall 31 or may be formed integrally with the distal end wall 31. In this case, the measurement gas is analyzed in a stable manner, and the filter 36 is prevented from being clogged with dust.

The present examples and embodiments are to be considered as illustrative and not restrictive, and the invention is not to be limited to the details given herein, but may be modified within the scope and equivalence of the appended claims.

What is claimed is:

1. A gas analyzer apparatus comprising:
   a support tube including a distal portion adapted to be arranged in a flue through which gas flows;
   a gas sensor for detecting a predetermined chemical component contained in the gas and including a distal portion, fixed to the distal portion of the support tube, and a basal portion arranged in the support tube; and
   an air supply means for supplying cooling air for cooling the basal portion of the gas sensor into the support tube.

2. The gas analyzer apparatus according to claim 1, wherein the air supply means includes an air supply tube having a distal end with an opening arranged in the support tube, wherein cooling air is ejected from the opening of the distal end toward the basal portion of the gas sensor.

3. The gas analyzer apparatus according to claim 2, further comprising:
   a connector tube accommodated in the support tube and covering the distal end of the air supply tube and the basal portion of the gas sensor, wherein the connector tube includes a distal end, a basal end, and at least one air inlet that is formed at a position close to the basal end.

4. The gas analyzer apparatus according to claim 3, wherein the connector tube has at least one air outlet formed at a position corresponding to the basal portion of the gas sensor.

5. The gas analyzer apparatus according to claim 3, wherein the distal portion of the gas sensor is mated with a distal end wall of the support tube from an inner side of the support tube;
   the gas sensor is partially or entirely accommodated in the connector tube; and
   the connector tube and the gas sensor include an engagement structure for engaging the connector tube and the gas sensor with each other so as to rotate integrally.

6. The gas analyzer apparatus according to claim 5, wherein the engagement structure includes:
   a sensor nut formed on an outer surface of the gas sensor; and
   a fitting structure formed in the connector tube for receiving the sensor nut.

7. The gas analyzer apparatus according to claim 1, further comprising:
   a sensor attachment member removably attached to the distal portion of the support tube, with the gas sensor being removably attached to the sensor attachment member.

8. The gas analyzer apparatus according to claim 7, wherein the distal portion of the support tube includes an open end, and the sensor attachment member is removably attached to the open end of the support tube.

9. The gas analyzer apparatus according to claim 8, wherein the sensor attachment member includes a distal end with an inlet for drawing in gas from the flue, the gas analyzer apparatus further comprising:
   a cap removably supported on the sensor attachment member, wherein the cap includes a wall projecting outward from the distal end of the sensor attachment member and being arranged upstream from the inlet of the sensor attachment member with respect to the flow of the gas.

10. The gas analyzer apparatus according to claim 9, wherein the cap includes a socket fitted to the sensor attachment member, and the socket and the sensor attachment member have an engagement structure for adjusting the position at which the cap is supported on the sensor attachment member.

11. The gas analyzer apparatus according to claim 10, wherein the engagement structure includes:
   a first hole formed in the socket;
   a plurality of second holes formed in the sensor attachment member; and
   an engagement member engaged with the socket and received in the first hole of the socket and a selected one of the plurality of second holes when the socket is fitted to the sensor attachment member.

12. The gas analyzer apparatus according to claim 11, wherein the plurality of second holes are formed in an outer surface of the sensor attachment member at predetermined intervals in a circumferential direction of the sensor attachment member.

13. The gas analyzer apparatus according to claim 11, wherein the engagement member does not project from an outer surface of the socket.

* * * * *